United States Patent [19]

Peeters et al.

[11] Patent Number: 4,932,405
[45] Date of Patent: Jun. 12, 1990

[54] SYSTEM OF STIMULATING AT LEAST ONE NERVE AND/OR MUSCLE FIBRE

[75] Inventors: Stefaan Peeters, Aartselaar; William A. S. Bosiers, Antwerp; Jacques Kinsbergen, Boechout, all of Belgium

[73] Assignee: Antwerp Bionic Systems N.V., Deurne, Belgium

[21] Appl. No.: 82,548

[22] Filed: Aug. 7, 1987

[30] Foreign Application Priority Data

Aug. 8, 1986 [NL] Netherlands ......................... 8602043

[51] Int. Cl.⁵ ......................... A61N 1/00; H05G 0/00
[52] U.S. Cl. ............................... 128/419 R; 128/420.6
[58] Field of Search .................... 128/419 R, 421, 903, 128/420.6, 420.5

[56] References Cited

U.S. PATENT DOCUMENTS

| Re. 26,809 | 3/1970 | Hagfors | 128/784 |
| 4,142,532 | 3/1979 | Ware | 128/419 P |
| 4,314,562 | 2/1982 | Ware | 128/419 P |
| 4,532,930 | 8/1985 | Crosby et al. | 128/421 |
| 4,592,359 | 6/1986 | Galbraith | 128/419 R |
| 4,606,329 | 8/1986 | Hough | 128/421 |
| 4,612,915 | 9/1986 | Hough et al. | 128/421 |
| 4,741,340 | 5/1988 | Batina et al. | 128/903 |

FOREIGN PATENT DOCUMENTS 2134335 8/1984 United Kingdom .

OTHER PUBLICATIONS

I.E.E.E. Spectrum, vol. 1, No. 1, Jan. 1984.

Primary Examiner—Francis Jaworski
Assistant Examiner—George Manuel
Attorney, Agent, or Firm—Birch, Stewart, Kolasch & Birch

[57] ABSTRACT

A system is described for stimulating a nerve or a muscle fibre of a living body including a hearing nerve in the cochlea. The system includes an implant and an electrode for stimulating the nerve or the fibre, which electrode is connected to the implant. To supply electrical power to the implant, a small transformer is used, of which one coil is implanted into the body and the other is outside the body but in the vicinity of the implanted coil. Where the system is used to enhance hearing, the implanted coil is selectively positioned around the auditory duct and the outer coil is inserted into the duct, so that both coils are substantially coaxial. For supplying information to the implant, infrared transmission through the skin is used, wherein the transmitter is provided adjacent to the skin and the receiver on the outside of the body.

11 Claims, 3 Drawing Sheets

SYSTEM OF STIMULATING AT LEAST ONE NERVE AND/OR MUSCLE FIBRE

BACKGROUND OF THE INVENTION

The present invention relates to a system of stimulating at least one nerve and/or muscle fibre of an animate subject.

An example of such a stimulating system for stimulating auditory nerves of a human being is known from IEEE Spectrum, volume 21, No. 1, Jan. 1984. In this known system a receiving unit mounted in the neighborhood of the ear of a sensory or cochlear deaf person includes a microphone to "hear" or capture sounds existing around the deaf person and a speech processing unit spaced from the ear and connected to the transmitting unit for processing the received sounds and for modulating waves for transmission by the transmitting unit to the implanted receiving section.

SUMMARY OF THE INVENTION

The present invention has for its object to provide a more accurate and versatile stimulating system.

The objects of the present invention are fulfilled by providing an information supply means according to the present invention having a receiver for radio frequency waves, but preferably a detector for infrared radiation; the power supply means can includes one or more batteries, but preferably includes receiving means for radio frequency waves.

A search of prior art disclosed the following references:
US-A-4.314.562,
IEEE Spectrum, volume 21, No. 1, Jan. 1984,
US-A-4.142.532,
DE-A-28 23 798,
GB-A-2.134.335,
US-E-26809.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE DRAWINGS

Figure 1:
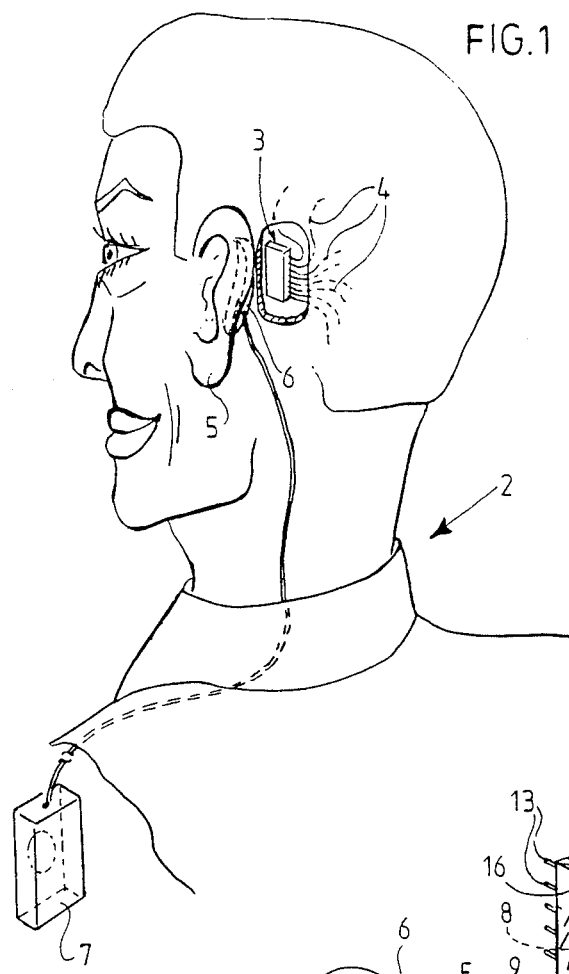
FIG. 1 a perspective view of a deaf subject provided with an implant according to the present invention.

An individual 2 (FIG. 1, 2) is provided with an implant 3 for stimulating nerves (and/or muscle fibres) as is shown by curved broken lines 4. The implant 3 is supplied with energy and information by a transmitting member 6 provided behind the ear flap or oracle 5, said transmitting member is fed by a signal processor 7 which processes sound received by a microphone (not shown).

Figure 2:
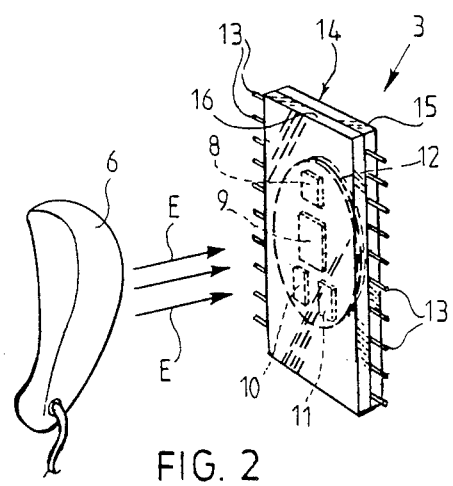
FIG. 2 a perspective and diagrammatic view of the transfer of electro-magnetic waves to the implant of FIG. 1.

The implant 3 (FIG. 2) is provided with electronic components 8, 9, 10, 11 respectively and a coil or antenna 12. Electrical connections 13 of platinum or platinum iridium are used for supplying the required signals to an electrode. Arrows E show the radiated electromagnetic energy, in which sound information is encoded.

A package 14 of the implant 3 consists of e.g. two casing parts 15 and 16 of biocompatible glass, for example Borosilicate or lime glass of the Hermetronics Company from Slough in England. The parts 15 and 16 are sealed in a biocompatible way, e.g. by means of adhesive, laser welding, resist welding, ultrasonic welding or hot cap sealing. Conducts of the connections 13 through the package 14 are sintered.

In the package 14 helium gas can be inserted, such that by means of a helium sniffer the seal can be checked on hermeticity. It is also possible not to bring this package into an atmosphere consisting of helium or another gas during some time period and afterwards to check for hermeticity outside this atmosphere (see e.g. Vakuum Technik, Rudolf A. Lang Verlag, 627 Idstein, 23 (1974) volume 3, pages 77–80). A hermeticity of $10^{-8}$ mbar.l/s can easily be achieved; this is sufficient for implantation in the human or other living body.

Figure 3:
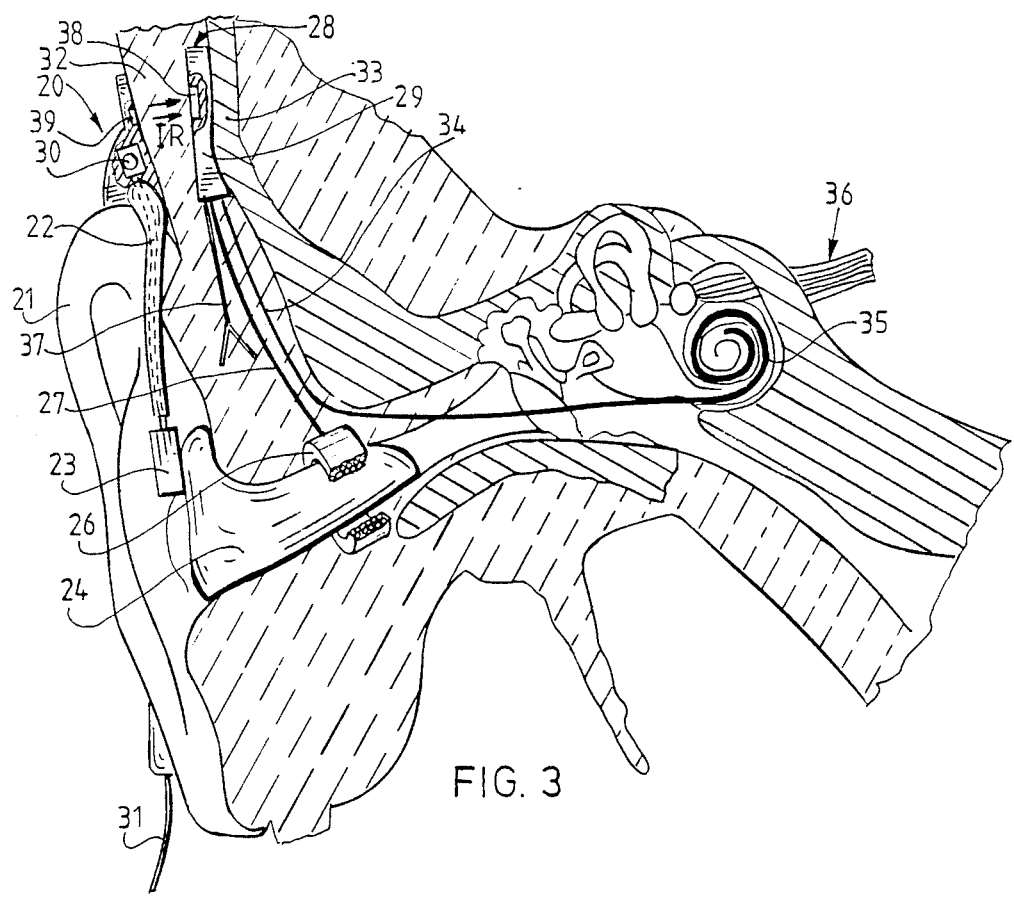
FIG. 3 a view partly in section, partly in perspective of another preferred embodiment of the stimulating system of the present invention.

In another preferred embodiment of the present invention (FIG. 3) an ear piece 20 which has the traditional shape to fit easily behind the ear 21 of a subject is provided with a lead 22 for connection at 23 to a rod shaped ear piece or mold 24, e.g. of plastic material and formed such as to be inserted into the auditory duct of the subject. This ear mold 24 includes a (not shown) coil or inductor to be coupled with an inductor 26 to be implanted around the auditory duct 25. Preferably this inductor or coil 26—diameter and height e.g. 2 mm, diameter of the windings e.g. 0.7 mm—is conically shaped, such as to fit around the inwardly tapering duct 25. The coil 26 is made flexible by means of a layer of silicon around the windings, such as to prevent painful contact after implantation between the ear piece 24 and coil 26.

By using the auditory duct 25 as a site for transferring energy into the body of the subject, by means of radio frequency waves, e.g. of a frequency of 100–500 kHz, accurate alignment between the two inductors will always be provided. Inductor or coil 26 is connected by means of line 27 to implant 28 which consists of a housing 29 of titanium provided with a window 38 of glass or transparant plastic or ceramic material.

The ear piece 20 is provided with a microphone 30. Electrical signals supplied by this microphone are fed through line 31 to a not shown speech processor (see e.g. FIG. 2). This speech processor encodes information as required by the implant. This information is fed from the ear piece 20 opposite to the window 38 by means of a infrared radiation emitting element 39 (IR-transmitter) to the implant 28. This infrared radiation emitting element 39 is contacted directly to the skin. Although it appears from experiments that 30% or even 10% of this infrared radiation is lost in the tissue 32 before reaching the window, the remaining part is sufficient to be detected behind the window 38 by means of an infrared radiation detector (IR-detector), without causing any damage to the tissue. The required power for the IR-detector is only a few $\mu$ Watt so that the emitting element 39 will emit e.g. a few mWatt of power, but more emitting power can be transmitted without damaging the animate tissue. The IR-transmitter and IR-detector are aligned in a natural way by means of the ear and traditionally shaped ear piece and mold; there is no significant anatomical spread in different ear locations. Also the implant can easily be secured to the skull 33 of the subject. Pulses can be transmitted at the high rate, pulses having a width of less than 400 nsec are achievable.

From the implant 28 there is provided a lead 34 to an electrode 35 which is to be implanted in the cochlea of the deaf subject. The electrode 35 has branches (not shown) for stimulating different locations within the cochlea. The electrode is flexible and provided with a hook shaped end part (not shown) such as to be easily implantable into the cochlea by a surgeon. Stimulation is achieved through physiological fluid and nerve fibres 36. Also there is connected to the implant 28 an antenna 37, the function of which will be described hereinafter.

Power from the lead 27 (FIG. 4) is rectified in rectifier 40 and fed to a voltage supply 41, which supplies voltage to all the different functional blocks within broken line 42, as is indicated by arrows A. The functions within broken line 42 are included in a custom integrated circuit especially designed for the system of the present invention. The infrared radiation is detected by detector 43 and fed to input monitor 44; in case the pulse shape is not correct—e.g. if a spike occurs —, a signal is fed to reset 45 which resets the integrated circuit and prevents a stimulating current within the cochlea. A pulse accepted by the input monitor will be fed to a pulse sequence detection unit 46 which detects time intervals between pulses, as hereinafter will be more fully described. The first pulse determines at 46 the mode in which the system will operate, the second pulse determines at 48 which of eight channels 51–58 of the electrode 35 will be activated, while at 49 the magnitude or quantity of the chosen channel is determined. At 60 the shape of the stimulating pulse is chosen by mode unit 47. Mode measuring is also chosen by mode unit 47 at 61. In the measuring mode a signal is provided by output 62 to the antenna 37. Clock 32 provides clock signals for the circuit; the clock rate can be set before implantation between 250 nsec- 2 μsec. The clock is synchronized at receiving each next accepted pulse.

Figure 5:
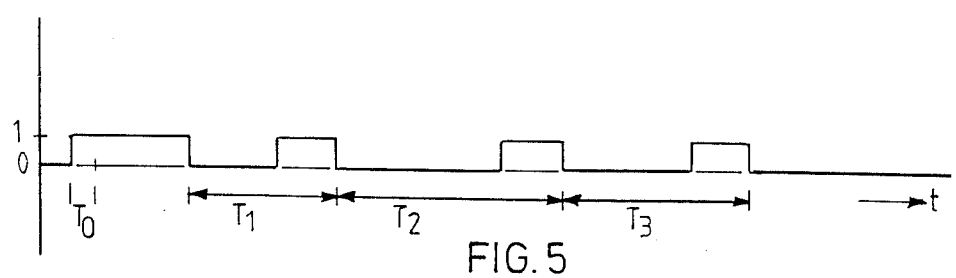
FIG. 5 an example of a signal arriving at the implant of FIG. 3.
Figure 4:
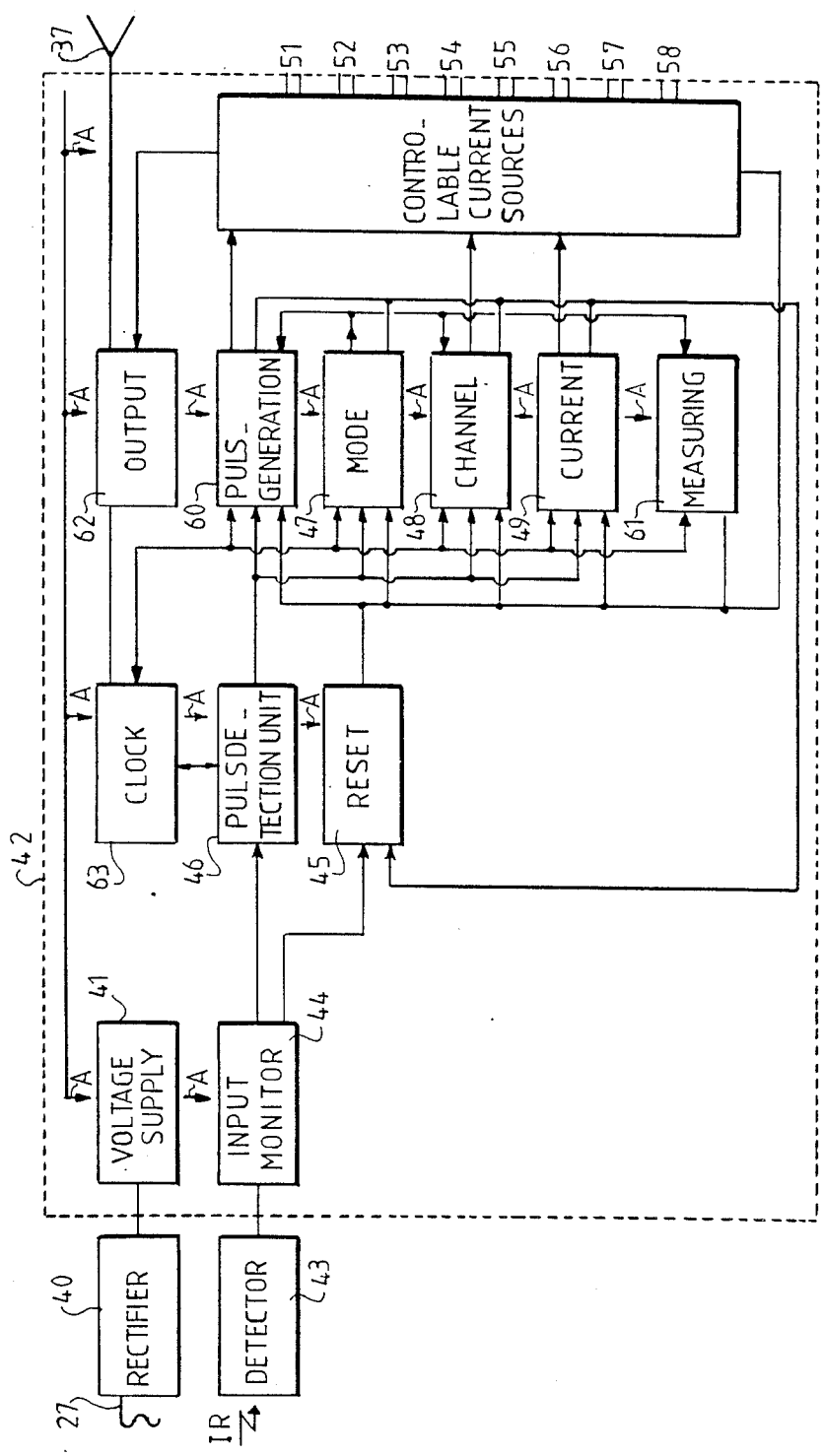
FIG. 4 a diagram illustrating the operation of the system of FIG. 4.

FIG. 5 shows an example of a pulse sequence to be transmitted by the ear piece and to be received by the IR-detector 43 (FIG. 4). $T_0$ is the period of one cycle of the clock 63 while $P_s$ designates the synchronizing pulse having a width of $4 \times T_0$; $T_1$ selects the mode (in this case biphasic see FIG. 6), which means that $T_1$ is between $2 \times T_0$ and $4 \times T_0$); $P_m$ stands for mode selection pulse and a duration of $2 \times T_0$; $T_2$ defines the channel to be activated, in this case channel 2, which means that $T_2$ is in between $4 \times T_0$ and $6 \times T_0$; $P_{ch}$ stands for channel selection pulse and has a duration of $2 \times T_0$; $T_3$ defines the strength of the stimulating pulse at channel 2, in this case e.g. 1,5 mA; $P_{cs}$ has a width of $2 \times T_0$.

Figure 6:
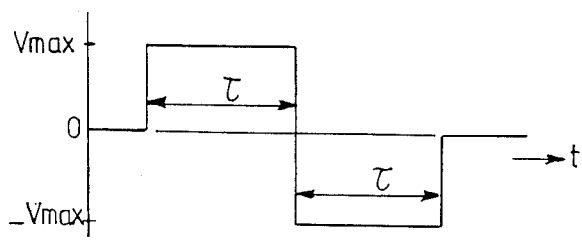
FIG. 6 an example of a stimulating signal.

FIG. 6 shows a biphasic pulse with a duration $\tau$ and extending between $V_{max}$ and $-V_{max}$ in which $\tau$ can be set before implantation and $V_{max}$ is determined by $T_3$. The biphasic pulse is symmetric around the zero-axis, such that no charge will build up in the cochlea of the subject. The inverse of FIG. 6 is called biphasic negative, in which the first edge of the pulse is going negative and the last edge is going downwardly. Other modes in which the system of the present invention can operate are so called normal modes (positive and negative) in which a constant current is supplied to two electrode branches, in which negative or positive decides which way the current will have to flow.

In the measuring mode there is supplied a measuring signal to the antenna, giving an indication of the supply voltage at 41 or the measured voltage at a selected electrode. The signals have e.g. a frequency of 1 MHz and can be detected outside the subject, such that the surveillance of correct operation of the implant can be established. When $T_1$, $T_2$ and $T_3$ have a relatively large value, the relative spread in those values is approximately held constant, such that the allowed absolute spread in values to be detected is increased.

The clock is only activated when the input monitor detects a synchronization pulse.

Reset unit 45 provides in resetting the circuit of FIG. 4 at missing one pulse, at erroneous detection of the synchronizing pulse, detection of decreasing power supply, and spikes occurring in the information supply. Therefore the described coding provides a very safe stimulating system, without inducing damaging current in an anminate body.

The shown preferred embodiment for stimulating auditory nerves of a subject has external parts outside the animate body which can be easily removed during such activities as swimming. It is expected that with this system a person having good functional auditory nerves will be able to comprehend speech.

As the system of the present invention uses coding in time sequence and the signal processing within the implant has a pipeline structure—not an operation according to the Von Neumann principle—a high rate of information transfer is achieved. IR-pulses can be made smaller than 400 nsec. At each sequence the implant is again synchronized and reset. The shown embodiments show systems for stimulating nerves, but the present invention can also be used for stimulating muscles, e.g. hard muscles.

The invention being thus described, it will be obvious that the same may be varied in many ways. Such variations are to to be regarded as a departure from the spirit and scope of the invention, and all such modifications as would be obvious to one skilled in the art are intended to be included within the scope of the following claims.

We claim:

1. A neural stimulating system for stimulating a selected nerve or muscle fiber, comprising:
   transmitting means adapted to be positioned outside the body of a subject for receiving sound waves and for generating a first and second signal representative of said sound waves, wherein said first and second signals are electromagnetic waves;
   receiving means adapted to be implanted in the body of said subject for receiving said first and second signals and, in response thereto, for generating an electric signal for stimulating said selected nerve or muscle fiber;
   inductor means for monitoring said second signal produced by said transmitting means and for converting said first signal into an electric signal for powering said receiving means, wherein said inductor means has an induction frequency in the range of 100–500 KiloHertz; and
   stimulating means, responsive to said receiving means, for stimulating said selected nerve or muscle fiber.

2. A neural stimulating system as received in claim 1, wherein:

said transmitting means further comprises infrared transmitting means for transmitting said second signal using infrared radiation; and said receiving means further comprises infrared detector means for detecting said second signal.

3. A neural stimulating system as recited in claim 1, wherein said receiving means encodes said first and second signals in a time sequence format.

4. A neural stimulating system as recited in claim 1, further comprising:

conductor means responsive to said first signal for conducting said first signal from said transmitting means to said inductor means.

5. A neural stimulating system as recited in claim 4, wherein said conductor means is adapted for insertion into the auditory canal of an ear.

6. A neural stimulating system as recited in claim 1, wherein:

said transmitting means further comprises microphone means for converting sound waves into said first and second signals.

7. A neural stimulating system as recited in claim 1, wherein said receiving means further comprises a housing, at least partly, made of biocompatible material.

8. A neural stimulating system as recited in claim 7, wherein said biocompatible material is glass.

9. A neural stimulating system as recited in claim 7, wherein said biocompatible material is ceramic.

10. A neural stimulating system as recited in claim 1, wherein said stimulation means further comprises an electronic means for adapted insertion into the cochlea of an ear of said subject, and once inserted, for adapted stimulating said selected nerve.

11. A neural stimulating system as recited in claim 7, wherein said housing is hermetically sealed.

* * * * *